(12) United States Patent
Reddy et al.

(10) Patent No.: US 10,059,678 B2
(45) Date of Patent: Aug. 28, 2018

(54) PROCESS FOR PREPARING OLODATEROL AND INTERMEDIATES THEREOF

(71) Applicant: G. Pratap Reddy, Telangana (IN)

(72) Inventors: G. Pratap Reddy, Telangana (IN); Venkataiah Sanku, Andhra Pradesh (IN)

(73) Assignee: G. Pratap Reddy, Telangana (IN)

( * ) Notice: Subject to any disclaimer, the term of this patent is extended or adjusted under 35 U.S.C. 154(b) by 0 days.

(21) Appl. No.: 15/510,147

(22) PCT Filed: Sep. 9, 2015

(86) PCT No.: PCT/IN2015/050104
§ 371 (c)(1),
(2) Date: Mar. 9, 2017

(87) PCT Pub. No.: WO2016/038628
PCT Pub. Date: Mar. 17, 2016

(65) Prior Publication Data
US 2017/0260149 A1    Sep. 14, 2017

(30) Foreign Application Priority Data
Sep. 9, 2014  (IN) .......................... 2876/MUM/2014

(51) Int. Cl.
C07D 265/36    (2006.01)
(52) U.S. Cl.
CPC ................................. *C07D 265/36* (2013.01)

(58) Field of Classification Search
CPC .................................................. C07D 265/36
See application file for complete search history.

(56) References Cited

U.S. PATENT DOCUMENTS

| | | |
|---|---|---|
| 4,460,581 A | 7/1984 | Schromm et al. |
| 8,420,809 B2 | 4/2013 | Krueger et al. |
| 2007/0088160 A1 | 4/2007 | Krueger et al. |
| 2010/0022770 A1 | 1/2010 | Rodriguez Dehli et al. |
| 2011/0124859 A1 | 5/2011 | Krueger et al. |

FOREIGN PATENT DOCUMENTS

| | | |
|---|---|---|
| WO | 2004087142 A1 | 10/2004 |
| WO | 2007020227 A1 | 2/2007 |

OTHER PUBLICATIONS

Bouyssou et al., "Discovery of Olodaterol, a Novel Inhaled β-Adrenoceptor Agonist with a 24 h Bronchodilatory Efficacy", Bioorganic & Medicinal Chemistry Letters, 2010, pp. 1410-1414, vol. 20, No. 4.
International Search Report for corresponding International PCT Application PCT/IN2015/050104, dated Mar. 23, 2016.

*Primary Examiner* — Paul V Ward
(74) *Attorney, Agent, or Firm* — Workman Nydegger

(57) ABSTRACT

The present invention relates to a process for preparing olodaterol and intermediates thereof. The process comprises of forming compound of Formula 1 by reacting compound of Formula 2 or its acid salt with compound of Formula 3 in the presence of an organic solvent to obtain compound of Formula 4. Protecting groups are removed from compound of Formula 4 in the presence of a suitable solvent to form compound of Formula 1.

20 Claims, No Drawings

PROCESS FOR PREPARING OLODATEROL AND INTERMEDIATES THEREOF

FIELD OF THE INVENTION

The present invention relates to a process for preparing beta adrenoceptor agonist and more particularly, to a process for preparing Olodoterol and intermediates thereof.

BACKGROUND OF THE INVENTION

Olodaterol hydrochloride is a beta-selective adrenoceptor agonist with potent bronchodilator activity. Olodaterol is chemically known as 6-hydroxy-8-[(1R)1-hydroxy-2-[2-(4-methoxy-phenyl)-1,1-dimethyl-ethylamino]-ethyl]-4H-benzo[1,4]oxazin-3-one. A particularly preferred pharmaceutically acceptable salt of olodaterol is olodaterol hydrochloride monohydrate.

The process for preparing Olodaterol is described in patents U.S. Pat. No. 4,460,581, US 2010022770 and US 2011124859. One of the key steps in the process is reacting an epoxide, such as 8-(2R)-oxiranyl-6-substitued oxy-4H-benzo[1,4]oxazin-3-one [Formula (I)] with an amine, such as 2-methyl-1-(4-methoxy-phenyl)-2-propanamine [Formula (II)] to form an intermediate 6-substituted oxy-8-[(1R)-1-hydroxy-2-[[2-(4-methoxy-phenyl)-1,1-dimethyl-ethyl]-amino]-ethyl]-4H-benzo[1,4]oxazin-3-one [Formula (IIIa)].

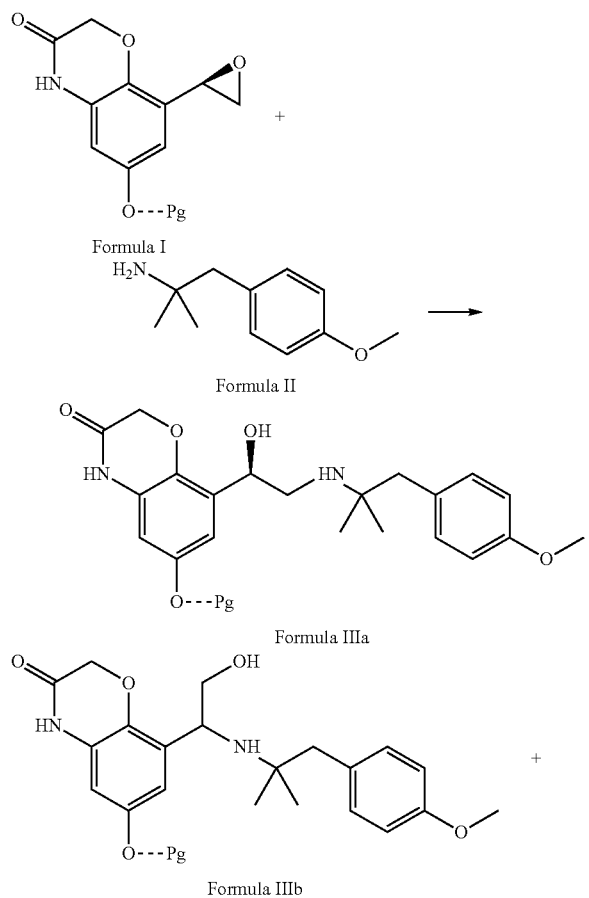

Formula I

Formula II

Formula IIIa

Formula IIIb

Formula IIIc

The drawback of this process is that the opening of epoxide ring is not regioselective and thereby resulting in formation of substantial quantities of impurities as by products, Formula (IIIb) and Formula (IIIc), resulting in overall lower yields. The quantity of 2-methyl-1-(4-methoxy-phenyl)-2-propanamine used in this step is also large excess than theoretical amounts.

Accordingly, there is a need for developing a more efficient process for preparing Olodaterol salts especially for large scale production with higher yields.

SUMMARY OF THE INVENTION

Accordingly, the present invention teaches a process for preparing 6-hydroxy-8-[(1R)1-hydroxy-2-[2-(4-methoxy-phenyl)-1,1-dimethyl-ethylamino]-ethyl]-4H-benzo[1,4]oxazin-3-one also known as olodaterol. The process comprises reacting compound of Formula 2 or its acid salt with compound of Formula 3 in the presence of an organic solvent to obtain compound of Formula 4. Protecting groups are removed from compound of Formula 4 in the presence of a suitable solvent to form compound of Formula 1.

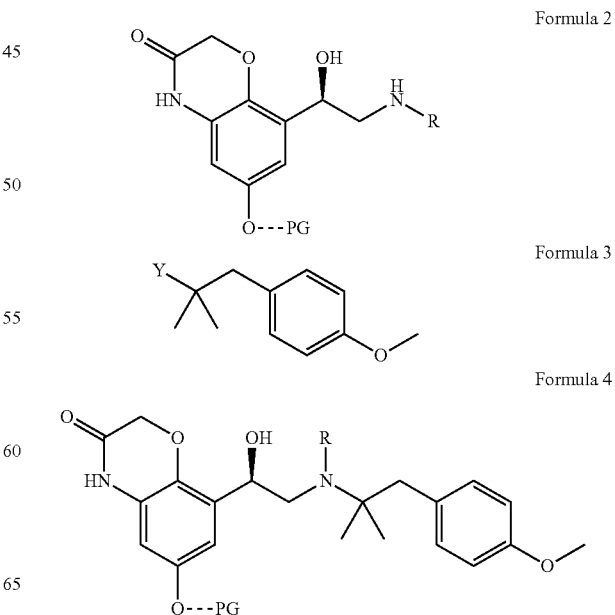

Formula 2

Formula 3

Formula 4

-continued

Formula 1

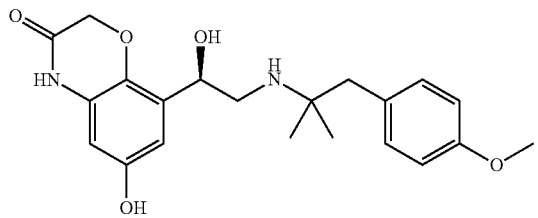

wherein,

Y is a leaving group

PG is a hydroxy protecting group

R is H or amine protecting group

The present invention also relates to compound of Formula 2.

Formula 2

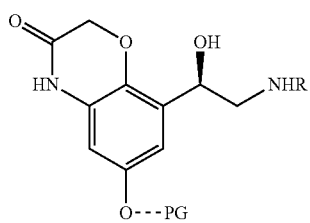

wherein,

PG is a hydroxy protecting group

R is H or amine protecting group

The present invention also relates to a process of preparing compound of Formula 2. The process comprises of reacting compound of Formula 6 with compound of Formula 7 in the presence of an organic solvent to form compound of Formula 8. Further, compound of Formula 8 is reacted with a reducing agent in the presence of a catalyst to form compound of Formula 9 followed by treatment with an amine deprotecting agent to obtain compound of Formula 10. Compound of Formula 10 is then treated with compound having an amine protecting agent to get a compound of Formula 2.

Formula 6

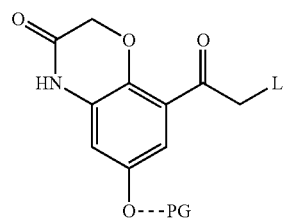

Formula 7

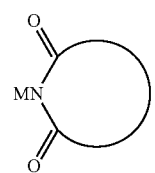

-continued

Formula 8

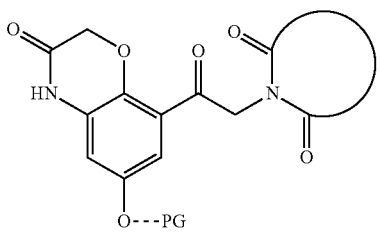

Formula 9

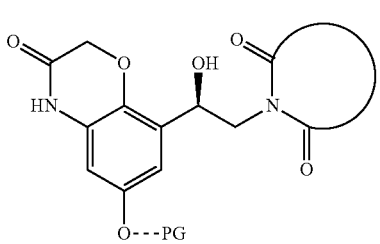

Formula 10

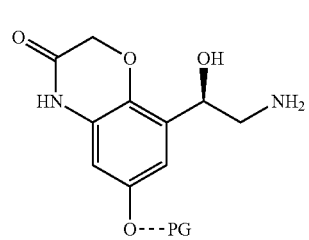

Formula 2

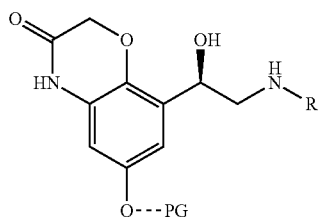

wherein,

L is a leaving group

PG is a hydroxy protecting group

M is H or alkali metal ion

R is H or amine protecting group

The present invention also provides another process of preparing compound of Formula 2. The process comprises of reacting compound of Formula 12 with compound of Formula 7 in the presence of an organic solvent to obtain compound of Formula 13. Further, the nitro group in the compound of Formula 13 is reduced to obtain a compound of Formula 14. Compound of Formula 14 is reacted with chloroacetyl chloride in the presence of an organic solvent to obtain compound of Formula 8. Further, compound of Formula 8 is reacted with a reducing agent in the presence of a catalyst to form compound of Formula 9 followed by treatment with an amine deprotecting agent to obtain compound of Formula 10. Compound of Formula 10 is then treated with compound having an amine protecting agent to get a compound of Formula 2.

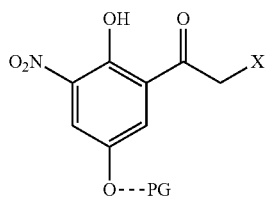

Formula 12

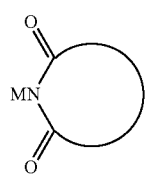

Formula 7

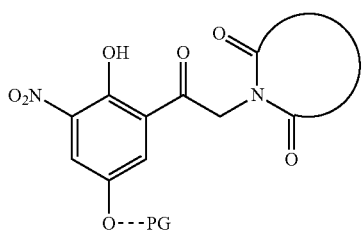

Formula 13

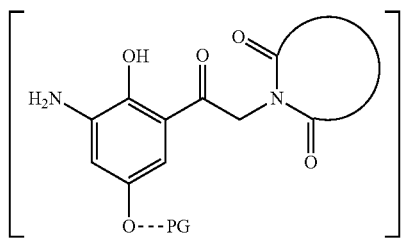

Formula 14

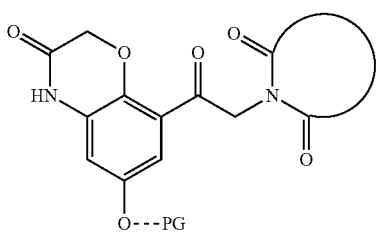

Formula 8

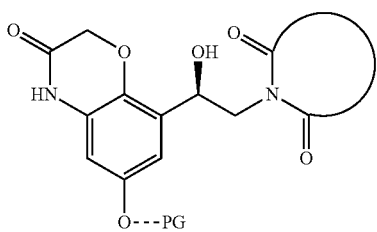

Formula 9

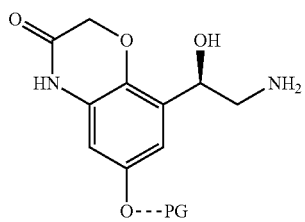

Formula 10

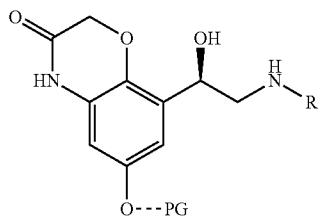

Formula 2 wherein,

PG is hydroxy protecting group

X is a leaving group

M is hydrogen or alkali metal ion

R is H or amine protecting group

DETAILED DESCRIPTION OF THE INVENTION

An embodiment of the present invention relates to a process for preparing 6-hydroxy-8-[(1R)1-hydroxy-2-[2-(4-methoxy-phenyl)-1,1-dimethyl-ethylamino]-ethyl]-4H-benzo[1,4]oxazin-3-one of Formula 1. The process comprises reacting compound of Formula 2 or its acid salt with compound of Formula 3 in the presence of an organic solvent to obtain a compound of Formula 4. The compound of Formula 4 can be isolated as a free base or its acid addition salts. The temperature of the reaction is maintained in a range of 0° C. to 120° C. Further, the protecting groups from the compound of Formula 4 are removed in the presence of an organic solvent to form 6-hydroxy-8-[(1R)1-hydroxy-2-[2-(4-methoxy-phenyl)-1,1-dimethyl-ethylamino]-ethyl]-4H-benzo[1,4]oxazin-3-one of Formula 1.

Compound of Formula 2 or its acid salt can be treated with compound of Formula 3 optionally in the presence of a base to form compound of Formula 4. An inorganic or an organic base is selected from alkali and alkali earth metal carbonate, bicarbonate, hydroxide, hydride, alkoxide, tertiary amines, N-methyl morpholine, N,N diisopropyl N-ethylamine, N-methyl piperidine, N-methyl pyrrolidine, 1,8-Diazabicyclo[5.4.0]undec-7-ene, 1,4-Diazabicyclo[2.2.2]octane.

The reaction scheme of preparing compound of Formula 1 is represented below:

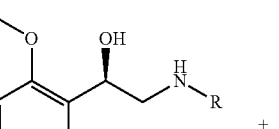

Formula 2

Formula 3

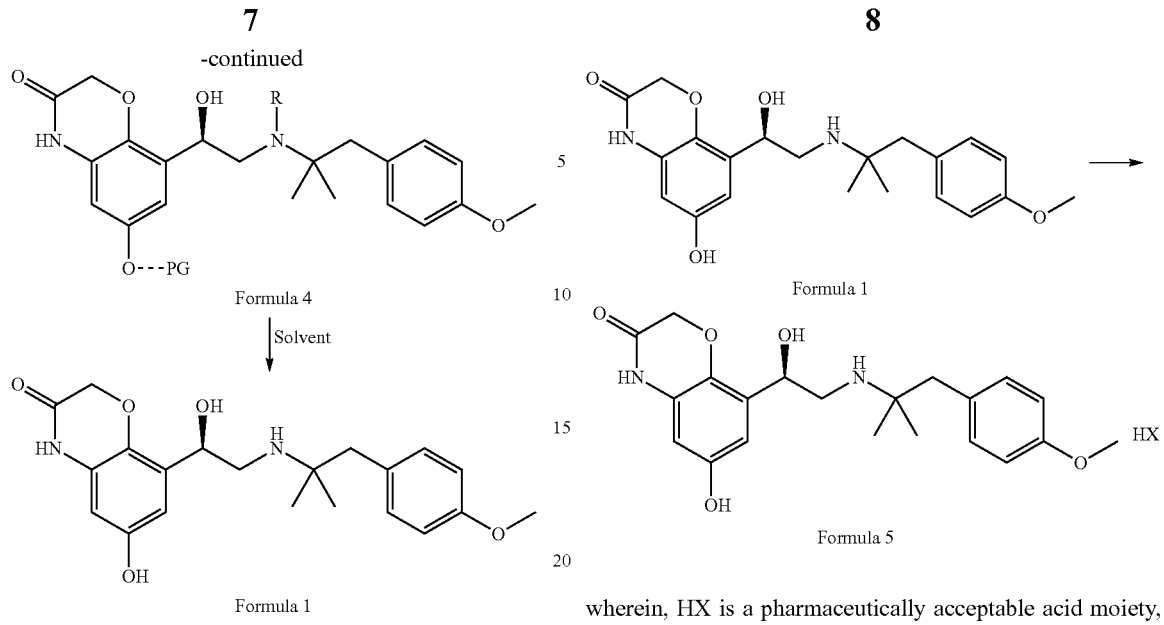

Formula 4

↓ Solvent

Formula 1

The leaving group Y in Formula 3 is selected from chloro, bromo, iodo, mesylate, tosylate, alkyloxy, aryloxy, acyloxy, silyloxy derivative, tetrahydropyranyloxy.

Group PG in compound of Formula 2 and Formula 4 is a hydroxy protecting group selected from arylalkoxy, alkyl, aryl, alkoxy, alkenyl, cycloalkyl, benzocycloalkyl, aralkyl, heterocyclic, heteroaralkyl, haloalkyl, and a substituted silyl group. In one embodiment, where protecting group is benzyl, preferred method of removing benzyl groups from compound of Formula 4 is by treating with hydrogen in the presence of a catalyst selected from the group consisting of palladium, palladium deposited on a suitable support, palladium hydroxide, platinum, platinum deposited on a suitable support and Raney-Nickel. Most preferably, the catalyst is palladium on carbon.

Group R in compound of Formula 2 and Formula 4 is H or an amine protecting group such as arylalkyl, alkyl or aryl carboxyl, alkoxycarbonyl and aryloxycarbonyl, preferably benzyl.

In a preferred embodiment of the present invention, compound of Formula 1 is treated with an acid in the presence of a solvent to form 6-hydroxy-8-[(1R)1-hydroxy-2-[2-(4-methoxy-phenyl)-1,1-dimethyl-ethylamino]-ethyl]-4H-benzo[1,4]oxazin-3-one salt of Formula 5. Acids such as oxalic acid, tartaric acid, maleic acid, fumaric acid, succinic acid, hydrochloric acid, sulphuric acid, and phosphoric acid are used to prepare compound of Formula 5.

The solvent used in the reactions is selected from $C_{1-6}$ straight chain or branched alcohols such as methanol, ethanol, isopropanol, tertiary-butyl alcohol, halogenated hydrocarbons such as dichloromethane, ethylene dichloride, chloroform, ketones such as acetone, methyl ethyl ketone, methyl isobutyl ketone, acetonitrile, ethers such as diethyl ether, diisopropyl ether, tetrahydrofuran, methyl tertiary-butyl ether, dioxane, mono- and di-alkyl ethyleneglycol ethers, aprotic solvents such as dimethyl sulfoxide, dimethylformamide, dimethylacetamide or mixtures thereof. More preferably, the solvent is methanol or ethanol.

The reaction scheme of preparing compound of Formula 5 from compound of Formula 1 is represented below:

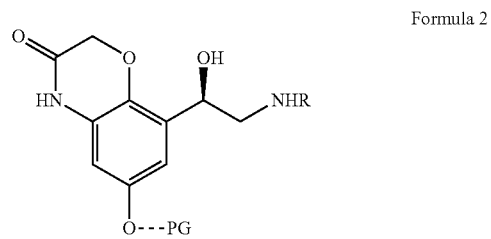

Formula 1

Formula 5 wherein, HX is a pharmaceutically acceptable acid moiety, preferably hydrochloride.

Another embodiment of the present invention relates to compound of Formula 2.

Formula 2

Group PG in compound of Formula 2 is a hydroxy protecting group selected from the group consisting of arylalkoxy, alkyl, aryl, alkoxy, alkenyl, cycloalkyl, benzocycloalkyl, aralkyl, heterocyclic, heteroaralkyl, haloalkyl, and a substituted silyl group.

Group R in compound of Formula 2 is H or amine protecting group such as arylalkyl, alkyl or aryl carboxyl, alkoxycarbonyl and aryloxycarbonyl, preferably benzyl.

In a preferred embodiment of the present invention, compound of Formula 2 is

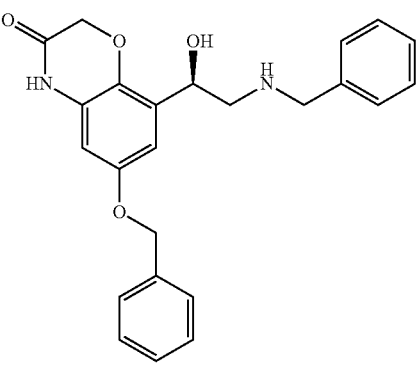 [SMILES: O=C1COc2c(cc(OCc3ccccc3)cc2[C@@H](O)CNCc2ccccc2)N1]

An embodiment of the present invention relates to a process for preparing compound of Formula 2. Compound of Formula 2 is prepared via two alternative ways.

Method A:

Compound of Formula 2 is prepared from compound of Formula 6. The process comprises of reacting compound of Formula 6 with compound of Formula 7 in the presence of an organic solvent to form compound of Formula 8. The temperature of the reaction is maintained in a range of 0° C. to 120° C. More preferably the temperature is 25° C. to 60° C. Further, compound of Formula 8 is reacted with a reducing agent in the presence of a catalyst to form compound of Formula 9 followed by treatment with an amine deprotecting agent to obtain compound of Formula 10. Compound of Formula 10 is then treated with an amine protecting agent to get a compound of Formula 2. In another embodiment, compound of Formula 10 can be used as such for the preparation of compound of Formula 1 without conversion to compound of Formula 2.

The step of reacting compound of Formula 6 with compound of Formula 7 in the presence of the organic solvent to form compound of Formula 8 is optionally carried out in the presence of a base. The base is inorganic or organic selected from alkali and alkali earth metal carbonate, bicarbonate, hydroxide, hydride, alkoxide, tertiary amines, N-methyl morpholine, N,N diisopropyl N-ethylamine, N-methyl piperidine, N-methyl pyrrolidine, 1,8-Diazabicyclo[5.4.0]undec-7-ene, 1,4-Diazabicyclo[2.2.2]octane. Preferably, sodium carbonate or potassium carbonate.

The organic solvent used in the reactions is selected from $C_{1-6}$ straight chain or branched alcohols such as methanol, ethanol, isopropanol, tertiary-butyl alcohol, halogenated hydrocarbons such as dichloromethane, ethylene dichloride, chloroform, ketones such as acetone, methyl ethyl ketone, methyl isobutyl ketone, acetonitrile, ethers such as diethyl ether, diisopropyl ether, tetrahydrofuran, methyl tertiary-butyl ether, dioxane, mono- and di-alkyl ethyleneglycol ethers, aprotic solvents such as dimethyl sulfoxide, dimethylformamide, dimethylacetamide or mixtures thereof. More preferably, the solvent is acetone.

Compound of Formula 7 is a cyclic imide having $C_4$-$C_5$ cyclic aliphatic ring, cyclic aliphatic ring fused with aromatic ring with or without substituents, cyclic aliphatic ring fused with heterocyclic ring with or without substituents, cycloalkenyl group.

The reducing agent is selected from the group consisting of sodium borohydride, borane-tetrahydrofuran complex, borane-dimethyl sulfide complex, borane-N,N,diethylaniline complex, diborane along with chiral catalyst selected from methyl-CBS, phenyl-CBS and 1-amino-2-indanol or hydrogenation in presence of Raney-Nickel or noble metals like Palladium, Platinum on charcoal.

In one embodiment, conversion of compound of formula 9 to Formula 10 can be carried out by using hydrazine hydrate or phenyl hydrazine in an organic solvent or reducing with sodium borohydride and hydrolyzing the intermediate with dilute acid, like hydrochloric acid, sulphuric acid or acetic acid.

The amine deprotecting agent is hydrazine hydrate or phenyl hydrazine in an alcohol, C1-C6 alcohol such as methanol, ethanol, propanol, butanol, pentanol and hexanol, or sodium borohydride.

The amine protecting agent is arylalkyl group, alkyl or aryl carboxyl, alkoxycarbonyl and aryloxycarbonyl, preferably benzyl.

The reaction scheme for synthesis of compound of Formula 2 by Method A is represented below:

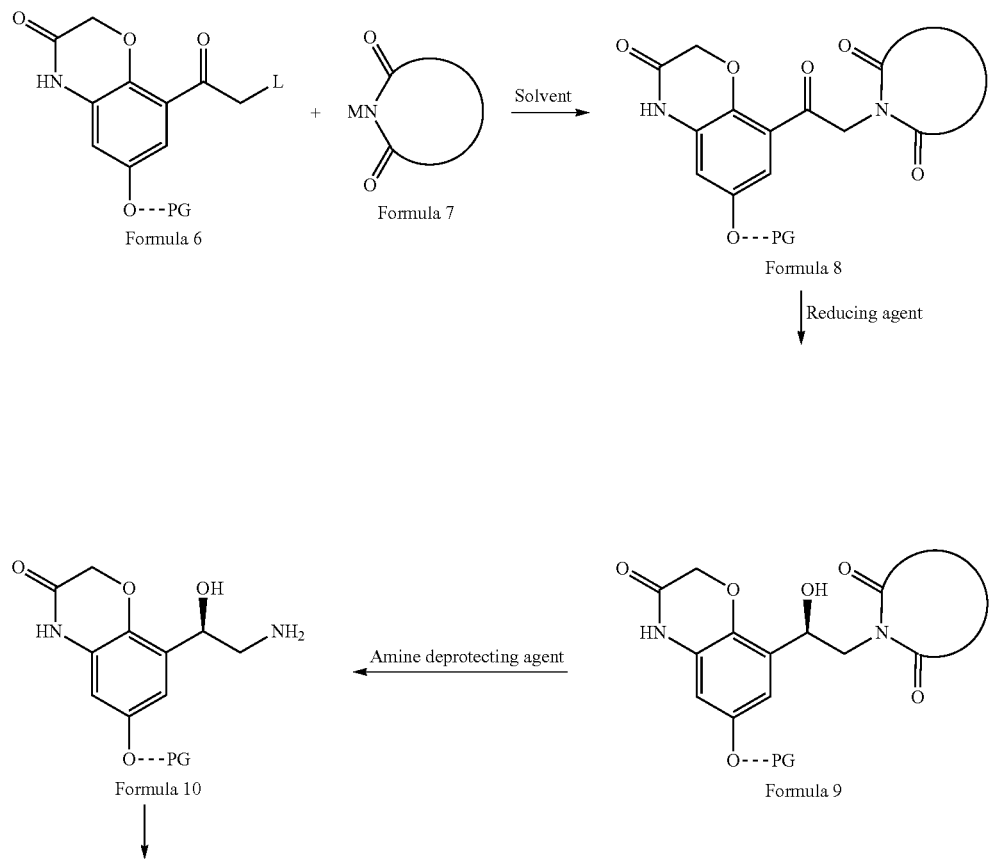

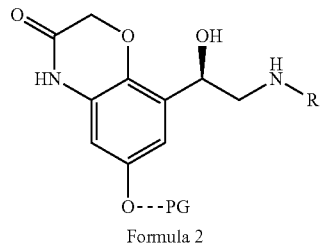

Formula 2

-continued

The leaving group L in Formula 6 is selected from chloro, bromo and iodo.

M in Formula 7 is hydrogen or an alkali metal selected from succinimide, phthalimide, and sodium, potassium or salts thereof. Preferably, phthalimide or succinimide.

Group R in compound of Formula 2 is H or amine protecting group such as arylalkyl, alkyl or aryl carboxyl, alkoxycarbonyl and aryloxycarbonyl, preferably benzyl.

Group PG in compound of Formula 2, Formula 6, Formula 8, Formula 9 and Formula 10 is a hydroxy protecting group is selected from the group consisting of arylalkoxy, alkyl, aryl, alkoxy, alkenyl, cycloalkyl, benzocycloalkyl, aralkyl, heterocyclic, heteroaralkyl, haloalkyl, and a substituted silyl group. Preferably, the protecting group is benzyl or t-butyldimethylsilyl.

Method B:

Compound of Formula 2 is prepared from compound of Formula 12. The process comprises of reacting compound of Formula 12 with compound of Formula 7 in the presence of an organic solvent to obtain compound of Formula 13. The temperature of the reaction is maintained in a range of 0° C. to about 120° C. More preferably the temperature is 25° C. to 60° C. Further, the nitro group in the compound of Formula 13 is reduced to obtain a compound of Formula 14. Compound of Formula 14 is reacted with chloroacetyl chloride in the presence of an organic solvent and a base to obtain compound of Formula 8. Further, compound of Formula 8 is reacted with a reducing agent in the presence of a catalyst to form compound of Formula 9 followed by treatment with an amine deprotecting agent to obtain compound of Formula 10. Compound of Formula 10 is then treated with an amine protecting agent to get a compound of Formula 2. In another embodiment, compound of Formula 10 can be used as such for the preparation of compound of Formula 1 without conversion to compound of Formula 2.

Compound of Formula 7 is a cyclic imide having $C_4$-$C_5$ cycloalkyl ring, cycloalkyl ring fused with aromatic ring with or without substituents, cycloalkyl ring fused with heterocyclic ring with or without substituents, cycloalkenyl group.

The base is inorganic or organic selected from alkali and alkali earth metal carbonate, bicarbonate, hydroxide, hydride, alkoxide, tertiary amines, N-methyl morpholine, N,N diisopropyl N-ethylamine, N-methyl piperidine, N-methyl pyrrolidine, 1,8-Diazabicyclo[5.4.0]undec-7-ene, 1,4-Diazabicyclo[2.2.2]octane. Preferably, sodium carbonate or potassium carbonate.

The organic solvent is selected from $C_{1-6}$ straight chain or branched alcohols such as methanol, ethanol, isopropanol, tertiary-butyl alcohol, halogenated hydrocarbons such as dichloromethane, ethylene dichloride, chloroform, ketones such as acetone, methyl ethyl ketone, methyl isobutyl ketone, acetonitrile, ethers such as diethyl ether, diisopropyl ether, tetrahydrofuran, methyl tertiary-butyl ether, dioxane, mono- and di-alkyl ethyleneglycol ethers, aprotic solvents such as dimethyl sulfoxide, dimethylformamide, dimethylacetamide or mixtures thereof. More preferably, the solvent is acetone.

The reducing agent is selected from the group consisting of sodium borohydride, borane-tetrahydrofuran complex, borane-dimethyl sulfide complex, borane-N,N,diethylaniline complex, diborane along with chiral catalyst selected from methyl-CBS, phenyl-CBS and 1-amino-2-indanol or hydrogenation in presence of Raney-Nickel or noble metals like Palladium, Platinum on charcoal.

The amine deprotecting agent is hydrazine hydrate or phenyl hydrazine in an alcohol, C1-C6 alcohol such as methanol, ethanol, propanol, butanol, pentanol and hexanol, or sodium borohydride.

The amine protecting agent is arylalkyl group, alkyl or aryl carboxyl, alkoxycarbonyl and aryloxycarbonyl, preferably benzyl.

The reaction scheme for synthesis of compound of Formula 2 by Method B is represented below:

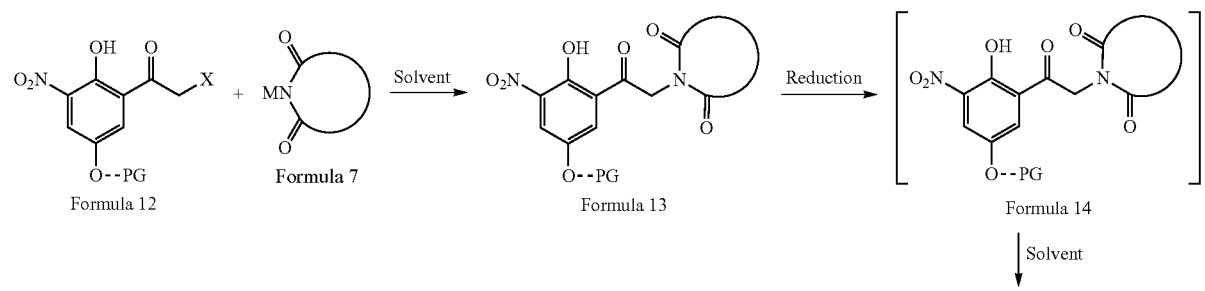

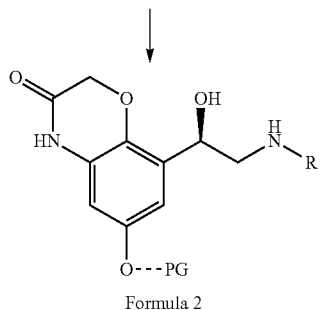

Formula 10

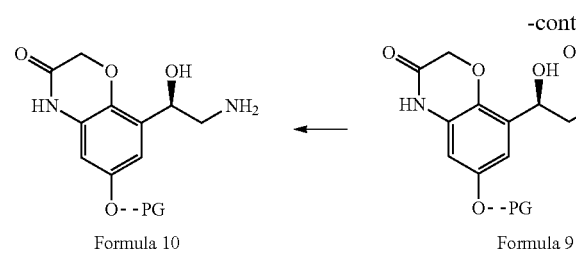

Formula 9

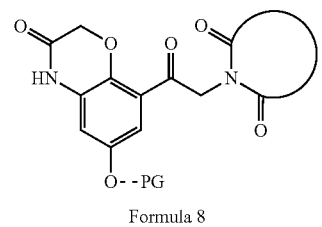

Formula 8

-continued

Amine deprotecting agent

Formula 2

The leaving group X in Formula 12 is selected from chloro, bromo, iodo, mesylate and tosylate.

M in Formula 7 is hydrogen or an alkali metal selected from succinimide, phthalimide, and sodium, potassium or salts thereof. Preferably, phthalimide or succinimide.

Group R in compound of Formula 2 is H or amine protecting group such as arylalkyl, alkyl or aryl carboxyl, alkoxycarbonyl and aryloxycarbonyl, preferably benzyl.

Group PG in compound of Formula 2, Formula 8, Formula 9, Formula 10, Formula 12, Formula 13, Formula 14 and Formula 10 is a hydroxy protecting group is selected from the group consisting of arylalkoxy, alkyl, aryl, alkoxy, alkenyl, cycloalkyl, benzocycloalkyl, aralkyl, heterocyclic, heteroaralkyl, haloalkyl, and a substituted silyl group. Preferably, the protecting group is benzyl or t-butyldimethylsilyl.

The process of the present invention results in formation of olodaterol salts having purity not less than 98% and ee more than 99%. The process of present invention provides olodaterol salts free of dimer and regioisomer therbey resulting in higher yields and simplifying the operations.

EXAMPLES

The following examples illustrate the invention, but are not limiting thereof.

Example 1

Method A: Process for Preparing 8-(2-phthalimido-1-oxo-ehthyl)-6-(phenylmethoxy)-2H-1,4-benzoxazin-3(4H)-one Potassium carbonate (34.5 g) was added to a suspension of phthalimide (31 g) in dimethylformamide (100 ml) at room temperature and stirred for 10 minutes. To this suspension, a solution of 8-(bromoacetyl)-6-(phenylmethoxy)-2H-1,4-benzoxazin-3 (4H)-one (75.5 g) in dimethylformamide (150 ml) was added slowly over a period of 20 minutes followed by sodium iodide (1 g). Then, the resulting suspension was stirred at 50-55° C. temperature for about 1 hour for the completion of reaction as monitored by TLC. The mixture was diluted with water (1000 ml) and the crude product was isolated by filtration. The wet filter cake was suspended in water (600 ml), stirred for 1 hour, filtered, washed with water and dried under vacuum to get 8-(2-phthalimido-1-oxo-ehthyl)-6-(phenylmethoxy)-2H-1,4-benzoxazin-3(4H)-one (83 g). Yield: 94%.

Method B: Process for Preparing 8-(2-phthalimido-1-oxo-ehthyl)-6-(phenylmethoxy)-2H-1,4-benzoxazin-3(4H)-one (a) To a suspension of phthalimide (31 g) and potassium carbonate (33 g) in dimethylformamide (300 ml), 2-bromo-1-[2-hydroxy-3-nitro-5-(phenylmethoxy)-phenyl]-ethanone (74 g) was added at room temperature followed by sodium iodide (1 g) and stirred for 2 hours. Then the temperature was raised to 50° C. and stirred for 1 hour for the completion of reaction as monitored by TLC. The mixture was diluted with water (1200 ml) and the crude product, 2-phthalimido-1-[2-hydroxy-3 nitro-5-(phenylmethoxy)-phenyl]-ethanone was isolated by filtration, washed and dried under reduced pressure. The crude product was taken for the next step.

(b) 2-Phthalimido-1-[2-hydroxy-3-nitro-5-(phenylmethoxy)-phenyl]-ethanone obtained in the above step was dissolved in 1,4-dioxane (1000 ml) and hydrogenated using Raney-Nickel catalyst (8 g) at 45° C. and at 4 bar hydrogen pressure until no more hydrogen was consumed. The mixture was cooled to room temperature and the catalyst was filtered off. To the clear filtrate, potassium carbonate (72 grams) and chloroacetyl chloride (30 g) were added and stirred at room temperature for 30 minutes. Then the mixture was heated to 60° C. and maintained there for the completion of reaction as monitored by TLC. The reaction mixture was cooled to room temperature and filtered. The clear filtrate was concentrated under reduced pressure. To the crude product, water (400 ml) was added, stirred for 30 minutes, filtered and dried under vacuum. Recrystallization from isopropanol yielded 8-(2-phthalimido-1-oxo-ehthyl)-6-(phenylmethoxy)-2H-1,4-benzoxazin-3(4H)-one (74 g). Overall yield: 84%

Example 2

Process for Preparing 8-[(R)-(2-phthalimido-1-hydroxy-ethyl)-6-(phenylmethoxy)-2H-1,4-benzoxazin-3(4H)-one To a solution of (R)-2-methyl-CBS-oxazaborolidine (1M in toluene, 11 ml) in dry tetrahydrofuran (THF, 150 ml), Borane-diethylaniline (50 ml) was added slowly at −10° C. and stirred the contents at the same temperature for 15 minutes. A solution of 8-(2-phthalimido-1-oxo-ehtyl)-6-(phenylmethoxy)-2H-1,4-benzoxazin-3 (4H)-one (22.2 g) of example 1, in a mixture of dry THF (120 ml) and dichloromethane (120 ml), was then added slowly to the reaction mass at −10 to −5° C. The reaction mass was further stirred for 2 hours and then methanol was added and the temperature was slowly raised to room temperature. Dilute sulfuric acid (6N, 26 ml) was added to the reaction mixture and stirred for 15 minutes. The reaction mixture was concentrated under vacuum and the crude mass was extracted with ethyl acetate. The organic phase was washed with dilute sulfuric acid and then with water. The solvent was distilled out completely under vacuum and triturated with hexane. The compound was isolated by filtration and dried (19.6 g). Yield: 88%; e.e. >97%.

Example 3

Process for Preparing 8-[(1R)-(2-amino-1-hydroxy-ethyl)-6-(phenylmethoxy)-2H-1,4-benzoxazin-3 (4H)-one To a solution of 8-[(1R)-(2-phthalimido-1-hydroxy-ethyl)-6-(phenylmethoxy)-2H-1,4-benzoxazin-3(4H)-one (44.5 g) in a mixture of isopropanol (270 ml) and water (35 ml), sodium borohydride (15.2 g) was added slowly at room temperature and stirred overnight. Thereafter, pH of the reaction mass was lowered to 5.5 with acetic acid, and then the reaction mass was heated to reflux for two hours. Isopropanol was distilled out under reduced pressure. The residue was diluted with ethyl acetate (400 ml) and concentrated hydrochloric acid (25 ml) was added and stirred for 15 minutes for the salts to precipitate out. The reaction mass was filtered and the salt was washed with ethyl acetate. To the clear filtrate, concentrated hydrochloric acid (35 ml) was added and stirred at 5°-10° C. for 30 minutes for 8-[(1R)-(2-amino-1-hydroxy-ethyl)-6-(phenylmethoxy)-2H-1,4-benzoxazin-3(4H)-one to separate out as hydrochloride salt. The product was isolated by filtration and dried under vacuum. The hydrochloride salt was dissolved in minimum amount of water and basified with sodium hydroxide solution. The product was isolated as free amine by concentrating the solution under reduced pressure and extracting the residue with isopropyl alcohol and distilling out the solvent (27 g). Yield: 86%.

Example 4

Process for Preparing 8-[(1R)-(2-benzylamino-1-hydroxy-ethyl)-6-(phenylmethoxy)-2H-1,4-benzoxazin-3 (4H)-one 8-[(1R)-(2-amino-1-hydroxy-ethyl)-6-(phenylmethoxy)-2H-1,4-benzoxazin-3(4H)-one (15.7 g) and benzaldehyde (6.2 g) were dissolved in absolute ethanol (90 ml) under reflux temperature. The solution was cooled to 0° C. and sodium borohydride (2 g) was added slowly. The reaction mass was stirred at room temperature for the completion of reaction. Thereafter, the reaction mass was acidified under cooling with 4N HCl and concentrated under reduced pressure. The residue was treated with aqueous ammonia to liberate the free base which was extracted with ethyl acetate. Solvent was distilled out and the product was isolated (18.8 g). Yield: 93%.

Example 5

Process for Preparing 6-(Phenylmethoxy)-8-[(1R)-1-hydroxy-2-[[2-(4-methoxyphenyl)-1,1-dimethyl-ethyl)]-amino]-ethyl]-2H-1,4-benzoxazin-3 (4H)-one To 8-[(1R)-(2-amino-1-hydroxy-ethyl)-6-(phenylmethoxy)-2H-1,4-benzoxazin-3(4H)-one (12.6 g) and 1-(4-methoxyphenyl)-2-methylpropan-2-yl methanesulfonate (11 g) in tetrahydrofuran (150 ml), sodium bicarbonate (5 g) was added and the reaction mass was stirred at 45° C. till the completion of reaction as monitored by TLC. Then the mixture was cooled to room temperature, filtered and concentrated under reduced pressure. The residue was diluted with ethanol (125 ml) and hydrochloric acid (5 g; 32%) was added at room temperature and stirred for 3 hours. The product was cooled to 20° C., filtered, washed with ethanol and dried under vacuum to get 6-(Phenylmethoxy)-8-[(1R)-1-hydroxy-2-[[2-(4-methoxyphenyl)-1,1-dimethyl-ethyl)]-amino]-ethyl]-2H-1,4-benzoxazin-3(4H)-one hydrochloride (18.9 g). Yield: 92%.

Example 6

Process for Preparing 6-Hydroxy-8-[(1R)-1-hydroxy-2-[[2-(4-methoxyphenyl)-1,1-dimethyl-ethyl)]-amino]-ethyl]-2H-1,4-benzoxazin-3 (4H)-one hydrochloride A solution of 6-(Phenylmethoxy)-8-[(1R)-1-hydroxy-2-[[2-(4-methoxyphenyl)-1,1-dimethyl-ethyl)]-amino]-ethyl]-2H-1,4-benzoxazin-3 (4H)-one hydrochloride (15 grams) in methanol (100 ml) was hydrogenated using Palladium on charcoal 5% (1.5 grams, as 50% wet) until the completion of reaction. The mixture was filtered over celite and the filtrate was concentrated at 40-45° C. under vacuum. The residue was diluted with hot isopropanol (50 ml, 50° C.). A mixture was stirred for 1 hour and then slowly cooled to 0-5° C. and stirred for 2 hours at the same temperature. The slurry was filtered, washed with cold isopropanol and dried under vacuum to get 6-Hydroxy-8-[(1R)-1-hydroxy-2-[[2-(4-methoxyphenyl)-1,1-dimethyl-ethyl)]-amino]-ethyl]-2H-1,4-benzoxazin-3 (4H)-one hydrochloride (10.9 g). Yield: 88%. Purity by HPLC: >98%. e.e. >99%.

Example 7

Process for Preparing 1-(4-methoxyphenyl)-2-methylpropan-2-ol

To a solution of 1-(4-methoxyphenyl)acetone (82 g) in a mixture of tetrahydrofuran (125 ml) and toluene (125 ml), methylmagnesium chloride (200 g; 3M solution in THF) was added slowly over a period of 45 minutes at 8-12° C. and stirred for 1 hour for the completion of reaction. Then the reaction solution was poured slowly into a mixture of toluene (150 ml) and 25% aqueous ammonium chloride solution (150 ml) at 20-25° C. and stirred for 15 minutes.

The layers were separated. Aqueous layer was extracted with toluene (50 ml). Combined organic layer was washed with water, brine and dried over anhydrous magnesium sulphate. The organic layer was concentrated under reduced pressure and the residue was diluted with n-heptane (300 ml), cooled to 0° C. and stirred for 2 hours. The product was isolated by filtration and dried under reduced pressure (84 g). Yield: 93%.

Example 8

Process for Preparing 1-(4-Methoxyphenyl)-2-methylpropan-2-yl methanesulfonate

To a solution of 1-(4-methoxyphenyl)-2-methylpropan-2-ol (90 g) and trimethylamine (61 g) in dichloromethane (300 ml), methanesolfonyl chloride (61 g) was added slowly at 0-5° C. over a period of 1 hour. The reaction mixture was stirred for 1 hour at the same temperature for the completion of reaction as monitored by TLC. Then, chilled water (200 ml) was added to the reaction mixture and stirred for 15 minutes. The organic layer was separated, washed with water and sodium bicarbonate solution, dried over anhydrous magnesium sulphate, and concentrated under reduced pressure to get 1-(4-methoxyphenyl)-2-methylpropan-2-ol (121 g). Yield: 94%.

The invention claimed is:

1. A process for preparing 6-hydroxy-8-[(1R)1-hydroxy-2-[2-(4-methoxy-phenyl)-1,1-dimethyl-ethylamino]-ethyl]-4H-benzo[1,4]oxazin-3-one of Formula 1, the process comprising:
   (i) reacting compound of Formula 2 or its acid salt with compound of Formula 3 in the presence of an organic solvent to obtain compound of Formula 4; and

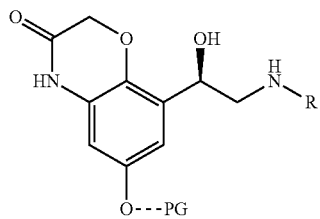

Formula 2

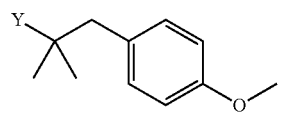

Formula 3

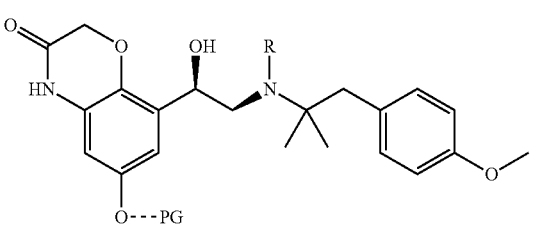

Formula 4 wherein,
Y is a leaving group
PG is a hydroxy protecting group
R is H or amine protecting group (ii) removing the protecting groups from the compound of Formula 4 in the presence of an organic solvent to form compound of Formula 1

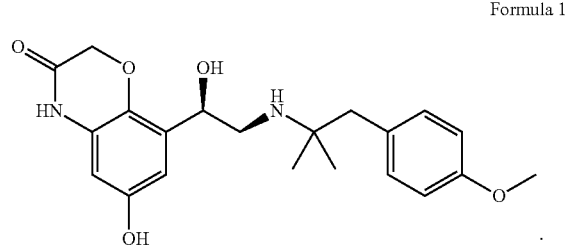

Formula 1

2. The process as claimed in claim 1 comprising treating the compound of Formula 1 with an acid in the presence of a solvent to form 6-hydroxy-8-[(1R)1-hydroxy-2-[2-(4-methoxy-phenyl)-1,1-dimethyl-ethylamino]-ethyl]-4H-benzo[1,4]oxazin-3-one salt of Formula 5;

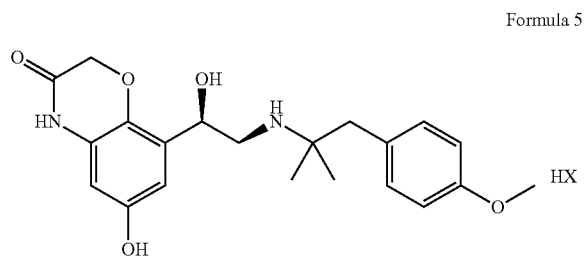

Formula 5 wherein, HX is a pharmaceutically acceptable acid moiety, preferably hydrochloride.

3. The process as claimed in claim 1, wherein step (i) is carried out in the presence of a base selected from the group consisting of alkali and alkali earth metal carbonate, bicarbonate, hydroxide, hydride, alkoxide, tertiary amines, N-methyl morpholine, N,N diisopropyl N-ethylamine, N-methyl piperidine, N-methyl pyrrolidine, 1,8-Diazabicyclo[5.4.0]undec-7-ene, and 1,4-Diazabicyclo[2.2.2]octane.

4. The process as claimed in claim 1, wherein the leaving group Y in Formula 3 is—chloro, bromo, iodo, mesylate, tosylate, alkyloxy, aryloxy, acyloxy, silyloxy derivative, or tetrahydropyranyloxy.

5. The process as claimed in claim 1, wherein the amine protecting group is arylalkyl group, alkyl or aryl carboxyl, alkoxycarbonyl or aryloxycarbonyl, preferably benzyl.

6. The process as claimed in claim 2, wherein acid is selected from the group consisting of oxalic acid, tartaric acid, maleic acid, fumaric acid, succinic acid, hydrochloric acid, phosphoric acid, sulfuric acid and phosphoric acid.

7. A process for preparing compound of Formula 2 as claimed in claim 1, the process comprising:
   (i) reacting compound of Formula 6 with compound of Formula 7 in the presence of an organic solvent to form compound of Formula 8;

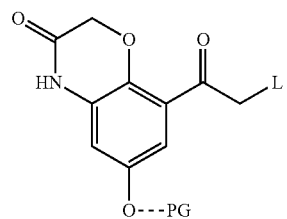

Formula 6

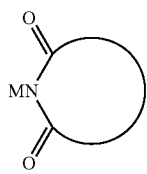

Formula 7

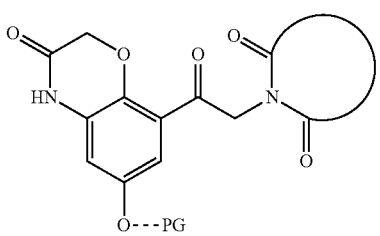

Formula 8 wherein,
L is a leaving group
PG is a hydroxy protecting group
M is H or alkali metal ion
  (ii) reacting compound of Formula 8 with a reducing agent in the presence of a catalyst to form compound of Formula 9;

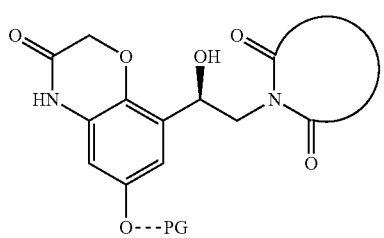

Formula 9 wherein, PG is a hydroxy protecting group
  (iii) treating compound of Formula 9 with an amine deprotecting agent to obtain compound of Formula 10; and

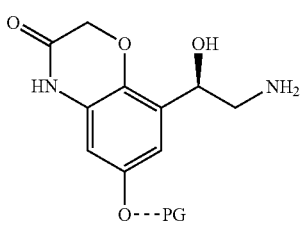

Formula 10 wherein, PG is a hydroxy protecting group
  (iv) reacting compound of Formula 10 with an amine protecting agent to get a compound of Formula 2

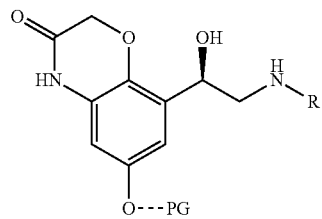

Formula 2 wherein,
PG is a hydroxy protecting group
R is H or amine protecting group.

8. The process as claimed in claim 7, wherein step (i) is carried out in the presence of a base selected from the group consisting of alkali and alkali earth metal carbonate, bicarbonate, hydroxide, hydride, alkoxide, tertiary amines, N-methyl morpholine, N,N diisopropyl N-ethylamine, N-methyl piperidine, N-methyl pyrrolidine, 1,8-Diazabicyclo[5.4.0]undec-7-ene, and 1,4-Diazabicyclo[2.2.2]octane.

9. The process as claimed in claim 7, wherein the reducing agent is selected from the group consisting of sodium borohydride, borane-tetrahydrofuran complex, borane-dimethyl sulfide complex, borane-N,N,diethylaniline complex, diborane along with chiral catalyst selected from methyl-CBS, phenyl-CBS and 1-amino-2-indanol or hydrogenation in presence of Raney-Nickel or noble metals like Palladium, and Platinum on charcoal.

10. The process as claimed in claim 7, wherein the leaving group L in Formula 6 is selected from the group consisting of chloro, bromo and iodo.

11. The process as claimed in claim 7, wherein compound of Formula 7 is a cyclic imide having $C_4$-$C_5$ cyclic aliphatic ring, cyclic aliphatic ring fused with aromatic ring with or without substituents, cyclic aliphatic ring fused with heterocyclic ring with or without substituents, cycloalkenyl group.

12. The process as claimed in claim 7, wherein M in Formula 7 is an alkali metal, sodium, potassium, and selected from succinimide, phthalimide, and or salts thereof.

13. The process as claimed in claim 1, wherein the temperature in step (i) is maintained in the range of 0° C. to 120° C.

14. The process as claimed in claim 7, wherein R is an amine protecting group, and the amine protecting group is selected from the group consisting of arylalkyl group, alkyl or aryl carboxyl, alkoxycarbonyl and aryloxycarbonyl, preferably benzyl.

15. The process as claimed in claim 7, wherein the amine deprotecting agent is hydrazine hydrate or phenyl hydrazine in an alcohol, $C_1$-$C_6$ alcohol such as methanol, ethanol, propanol, butanol, pentanol and hexanol, or sodium borohydride.

16. A compound of claim 1 having the structure of Formula 2

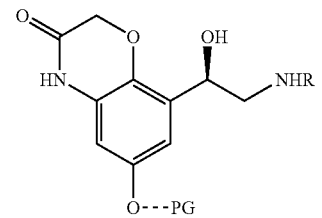

Formula 2 wherein,
PG is a hydroxy protecting group
R is H or amine protecting group.

17. The compound as claimed in claim 16, wherein the hydroxy protecting group PG is selected from the group consisting of arylalkoxy, alkyl, aryl, alkoxy, alkenyl, cycloalkyl, benzocycloalkyl, aralkyl, heterocyclic, heteroaralkyl, haloalkyl, and a substituted silyl group and the N-protecting group is arylalkyl preferably benzyl.

18. The compound of Formula 2 as claimed in claim 16, wherein the compound is Formula 2

19. A process for preparing compound of Formula 2, the process comprising:
  (i) reacting compound of Formula 12 with compound of Formula 7 in the presence of an organic solvent to obtain compound of Formula 13;

Formula 12

Formula 7

Formula 13 wherein,
PG is hydroxy protecting group
X is a leaving group
M is hydrogen or alkali metal ion
  (ii) reducing the nitro group in the compound of Formula 13 to obtain a compound of Formula 14;

Formula 14 wherein, PG is a hydroxy protecting group
  (iii) reacting compound of Formula 14 with chloroacetyl chloride in the presence of an organic solvent to obtain compound of Formula 8, Formula 8 wherein, PG is a hydroxy protecting group
  (iv) reacting compound of Formula 8 with a reducing agent in the presence of a catalyst to form compound of Formula 9;

Formula 9 wherein, PG is a hydroxy protecting group
  (v) treating compound of Formula 9 with an amine deprotecting agent to obtain compound of Formula 10; and Formula 10 wherein, PG is a hydroxy protecting group
  (vi) reacting compound of Formula 10 with an amine protecting agent to get a compound of Formula 2

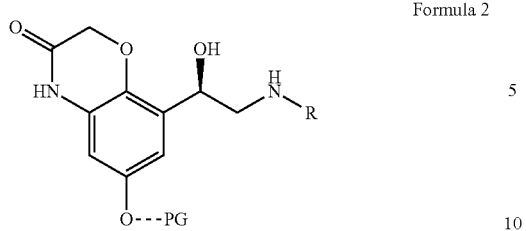
Formula 2
wherein,
PG is a hydroxy protecting group
R is H or amine protecting group.
20. The process as claimed in claim 19, wherein the temperature in step (i) is maintained in the range of 0° C. to 120° C.
* * * * *